(12) United States Patent
Tsaur et al.

(10) Patent No.: US 7,446,081 B2
(45) Date of Patent: *Nov. 4, 2008

(54) RINSE-OFF FACIAL WASH COMPOSITIONS DELIVERING ENHANCED WHITENING USING SUBMICRON TITANIUM OXIDE, OPTIONAL MODIFIER AND DEPOSITION SYSTEM

(75) Inventors: Liang Sheng Tsaur, Norwood, NJ (US); Jack Polonka, Peekskill, NY (US); Prem Chandar, Closter, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/997,179

(22) Filed: Nov. 24, 2004

(65) Prior Publication Data

US 2005/0227882 A1  Oct. 13, 2005

Related U.S. Application Data

(63) Continuation-in-part of application No. 10/814,879, filed on Mar. 31, 2004, now abandoned.

(51) Int. Cl.
*A61K 7/00* (2006.01)
(52) U.S. Cl. .................... 510/130; 510/139; 510/158; 510/159; 510/424; 510/470; 424/70.1; 424/70.9
(58) Field of Classification Search ................ 510/130, 510/139, 159, 424, 470, 473
See application file for complete search history.

(56) References Cited

U.S. PATENT DOCUMENTS

| | | | |
|---|---|---|---|
| 4,673,525 A | 6/1987 | Small et al. | |
| 5,076,953 A | 12/1991 | Jordan et al. | |
| 5,296,159 A | 3/1994 | Wilson et al. | |
| 6,759,376 B2 | 7/2004 | Zhang et al. | |
| 6,780,826 B2* | 8/2004 | Zhang et al. | 510/130 |
| 2003/0108501 A1* | 6/2003 | Hofrichter et al. | 424/70.1 |
| 2003/0109391 A1* | 6/2003 | Midha et al. | 510/122 |
| 2004/0087668 A1* | 5/2004 | Schmucker-Castner et al. | 516/90 |
| 2004/0186030 A1* | 9/2004 | Hofrichter et al. | 510/130 |
| 2004/0223993 A1* | 11/2004 | Clapp et al. | 424/401 |
| 2004/0234470 A1 | 11/2004 | Zhang et al. | |

FOREIGN PATENT DOCUMENTS

WO   97/29736   8/1997

OTHER PUBLICATIONS

U.S. Appl. No. 10/814,473, filed Mar. 31, 2004, Patel et al., (now abandoned), for: Beauty Wash Product Bar Compositons Delivering Enhaced Visual Benefits to the Skin With Specific Optical Attributes.
U.S. Appl. No. 10/997,180, filed Nov. 24, 2004, Patel et al., for: Beauty Wash Product Bar Compositons Delivering Enhaced Visual Benefits to the Skin With Specific Optical Attributes.
U.S. Appl. No. 11/043,315, filed Jan. 26, 2005, Patel et al., for: Beauty Wash Product Bar Compositons Delivering Enhaced Visual Benefits to the Skin With Specific Optical Attributes.
U.S. Appl. No. 10/815,003, filed Mar. 31, 2004, Polonka et al., (now abandoned), for: Beauty Wash Product Compositons Delivering Enhaced Visual Benefits to the Skin With Specific Optical Attributes.
U.S. Appl. No. 10/996,532, filed Nov. 24, 2004, Polonka et al., for: Beauty Wash Product Compositions Delivering Enhanced Visual Benefits to the Skin With Specific Optical Attributes.
U.S. Appl. No. 11/043,509, filed Jan. 26, 2005, Polonka et al., for: Beauty Wash Product Compositions Delivering Enhanced Visual Benefits to the Skin With Specific Optical Attributes.
U.S. Appl. No. 10/814,879, filed Mar. 31, 2004, Tsaur et al., (now abandoned), for: Rinse-off Facial Wash Compositions Delivering Enhanced Whitening Using Submicron Titanium Oxide, Optional Modifier and Deposition System.
U.S. Appl. No. 10/814,473, filed Mar. 31, 2004, Patel et al., (now abandoned), for: Beauty Wash Product Bar Compositons Delivering Enhaced Visual Benefits to the Skin With Specific Optical Attributes.
U.S. Appl. No. 10/997,180, filed Nov. 24, 2004, Patel et al., for: Beauty Wash Product Bar Compositons Delivering Enhaced Visual Benefits to the Skin With Specific Optical Attributes.
U.S. Appl. No. 11/043,315, filed Jan. 26, 2005, Patel et al., for: Beauty Wash Product Bar Compositons Delivering Enhaced Visual Benefits to the Skin With Specific Optical Attributes.
U.S. Appl. No. 10/815,003, filed Mar. 31, 2004, Polonka et al., (now abandoned), for: Beauty Wash Product Compositons Delivering Enhaced Visual Benefits to the Skin With Specific Optical Attributes.
U.S. Appl. No. 10/996,532, filed Nov. 24, 2004, Polonka et al., for: Beauty Wash Product Compositions Delivering Enhanced Visual Benefits to the Skin With Specific Optical Attributes.
U.S. Appl. No. 11/043,509, filed Jan. 26, 2005, for: Beauty Wash Product Compositions Delivering Enhanced Visual Benefits to the Skin With Specific Optical Attributes.
U.S. Appl. No. 10/814,879, filed Mar. 31, 2004, Tsaur et al., (now abandoned), for: Rinse-off Facial Wash Compositions Delivering Enhanced Whitening Using Submicron Titanium Oxide, Optional Modifier and Deposition System.

* cited by examiner

*Primary Examiner*—Necholus Ogden
(74) *Attorney, Agent, or Firm*—Ronald A. Koatz

(57) ABSTRACT

The present invention relates to facial wash compositions delivering enhanced whitening using sub-micron titanium dioxide, optional modifier and specific deposition systems.

7 Claims, No Drawings

RINSE-OFF FACIAL WASH COMPOSITIONS DELIVERING ENHANCED WHITENING USING SUBMICRON TITANIUM OXIDE, OPTIONAL MODIFIER AND DEPOSITION SYSTEM

RELATED APPLICATIONS

This application is a continuation-in-part of Ser. No. 10/814,879, filed Mar. 31, 2004, now abandoned.

FIELD OF THE INVENTION

The present invention relates to rinse-off cleanser compositions delivering immediate skin whitening effect. This is accomplished by using sub-micron titanium dioxide, preferably together with optical modifier (e.g., micron size mica or talc or emollient oil) from facial cleanser base. Generally, the enhancement is obtained by use of specific deposition system (e.g., cationic polymer/anionic surfactant precipitates) and/or by ensuring dispersion of particles (e.g., little or no agglomeration) onto skin or deposited substrate.

BACKGROUND

It is extremely difficult to deliver enhanced whitening, especially rapid whitening, from a rinse-off composition. The optical modifiers delivering these properties are not readily deposited, are readily rinsed of and, because they readily agglomerate, are not in a sufficiently dispersed state to be efficiently delivered to substrate (which is another way to say that they rinse off too easily).

Applicants' co-pending U.S. Ser. No. 10/241,401 to Zhang et al., filed Sep. 11, 2002 discloses personal care formulations comprising particles of defined refractive index, thickness, geometry and size. While this disclosure relates to how size, shape, etc. of the particles themselves help deposition (and thus shine), it fails to disclose specific deposition enhancement systems (e.g. based on type of surfactant and/or polymers), and the use of dispersed, sub-micron $TiO_2$ (preferably with other optical modifiers) to deliver enhanced whiteness. It also does not disclose how particles must be adequately dispersed on substrate (e.g., skin) to deliver defined change values needed to perceive measure optical traits.

U.S. Ser. No. 10/443,396 to Zhang et al., filed May 23, 2003 discloses structured benefit agent for enhanced delivery of optical modifier, but again does not disclose combination of sub-micron titanium dioxide, cationic deposition polymers (forming precipitates as deposition aid) and adequate dispersal to deliver enhanced whiteness.

BRIEF SUMMARY OF THE INVENTION

Unexpectedly, applicants have now found both compositions and ways to manipulate such compositions to provide enhanced whitening from rinse-off systems. That is, using deposition enhancement systems (e.g., characterized, for example, by precipitates formed through interaction of polymers and surfactants), modifiers associated with specified optical properties (e.g., sub-micron titanium dioxide for whiteness), can be dispersed and delivered to provide desired optical whiteness (i.e., by providing sufficient change in absolute or percentage values of the whitening component to result in perceived whitening changes). Changes in optical attributes previously unobtainable from wash-off/rinse-off systems are provided by selecting the specified components.

More particularly, the invention comprises as follows:

Beauty wash product compositions for delivery of enhanced (changed) whitening or brightening to the skin comprising:

a) from about 0.5% to about 90%, preferably 5 to 75% more preferably 10 to 75%, most preferably 20% to 70% by weight surfactant selected from anionic, nonionic, amphoteric and cationic surfactants and mixtures thereof.

b) from 0 to 35%, preferably 0.2 to 25% by weight of solid particulate optical modifier which exhibits a specific set of optical properties (e.g., defining radiance or shine (Δ gloss), whiteness (ΔL), degree of red or greenness (Δa*), degree of yellow or blueness (Δb*), change in opacity) and which, in combination with a deposition enhancement system, provides at least 5% improvement (i.e., 5% change) in at least one visual attribute being targeted (e.g., shine, color), wherein values reflecting various optical properties are measured before or after conducting tests according to a defined protocol, when said composition is applied to the skin;

c) from 0.01% to 30%, preferably 0.1 to 25% by wt. of titanium dioxide particles having size of about 100 nm to 300 nm d) from 0.1 to 25% by wt. of a deposition enhancement system, wherein, the deposition enhancement system enhances delivery to the skin of a target or defined visual attribute (i.e., whitening) by the optical modifier relative to a composition that has the same surfactant and optical modifier used at the same concentration but does not have the deposition enhancement system; and e) from about 0.1% to 45% of a hydrophilic structural dispersant (e.g., polyalkylene glycol).

The enhanced whiteness may be measured by a change in L value (measure of whiteness) of at least 5% in absolute or per cent terms.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances b the term "about". Similarly, all percentages are weight/weight percentages of the total composition unless otherwise indicated. Numerical ranges expressed the format "from x to y" are understood to include x and y. When for a specific feature multiple preferred ranges are described in the format "from x to y" it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to composition and to methods of delivering enhancement in delivery of whiteness from rinse-off compositions. Specifically, by using sub-micron titanium dioxide, preferably together with other optical modifiers, and specific deposition enhancement systems, a targeted value can be manipulated to deliver desired whiteness.

Specifically, the rinse-off compositions of the invention comprise:
- a) 0.5% to 90%, preferably 5% to 75%, more preferably 10% to 75% by wt. of a lathering surfactant (By lathering is meant the composition will have foam of at least 30 cc in a lather wash test);
- b) 0% to 35%, preferably 0.2% to 25% by wt. of a solid particulate optical modifier enhancing a specific set of properties (e.g. whiteness) and which, in combination with deposition enhancement system for the modifier (e.g. precipitate formed from interaction of polymer and surfactant) provides at least 5% change in at least one targeted visual attribute, wherein said change is defined by increase or decrease in absolute or percentage value characterizing a specific trait (i.e., Δ gloss is associated with radiance or ΔL with whiteness) and evaluation is made after using a defined in vitro skin protocol test;
- c) from 0.01% to 30% by wt. titanium dioxide particles having size of 100 to 300 nm;
- d) from 0.1 to 25% by wt. of said deposition enhancement system wherein, said system (c) is defined by its ability to enhance delivery of said targeted visual attribute, by the modifier relative to composition with some surfactant and modifier at same concentration, but which does not have the deposition enhancement system, and
- e) from 0.1 to 45% by wt. of a hydrophilic structural dispersant Surfactant is present at a level of 0.5 to 90%, preferably 5 to 75%, more preferably 10-75%, even more preferably 20% to 70% by wt. of composition, depending on product form.

In general, as noted, the surfactant may be selected from the group consisting of soap (including pure soap systems), anionic surfactant, nonionic surfactant, amphoteric/zwitterionic surfactant, cationic surfactant and mixtures thereof.

"Soap" is used is in the popular sense i.e., alkali metal or alkanol ammonium salts of aliphatic, alkane or alkene monocarboxylic acids. Other surfactants which may be used are described in "Surface Active Agents and Detergents" (Vol. I & II) by Schwartz, Perry & Berch, a copy of which is incorporated by reference into the subject application.

As indicated, the particulate optical modifier (titanium dioxide plus optional other modifier) should provide, in combination with deposition enhancement system, at least a 5% change in L value associated with lightening.

Specifically, improvement is measured by taking a value for a particular measured component (e.g., L value for whitening) and measuring (e.g., using in vitro pig assay) values of the components before and after application of particle deposition enhancement system.

The optical benefit carried by the deposition of optical modifier can be targeted to either plateaus on the skin surface or to skin crevices.

In one embodiment, the formulation deposition of $TiO_2$ and optional modifier creates skin lightening, whitening, and/or color or similar attributes and the composition deposits sub-micron $TiO_2$ and optional particulate optical modifier to exhibit ΔL value in the range of ±10 L units. Δa* values may be in the range from about 0 to about ±10, Δb* value may be in range from about 0 to about ±10, and a change in opacity may be in the range from about 0 to about ±50%. The reflectance should be within normal skin reflectancy range. In this case, this means change in reflectance is ≦10%. Although there may be a focus on Δa* and Δb* values (since there is a focus on general color attributes), it is important L value (associated with whitening) be changed at least 5%.

OPTICAL MODIFIER

The optional optical modifier which may be used for the subject invention may be chosen from non-colored and colored, organic and inorganic materials.

Among the materials which may be used are included:

Organic pigments, inorganic pigments, polymers and fillers such as titanium oxide, zinc oxide, colored iron oxide, chromium oxide/hydroxide/hydrate, alumina, silica, zirconia, barium sulfate, silicates, natural/alkaloid (including derivatives) polymers, polyethylene, polypropylene, nylon, ultramarine, alkaline earth carbonates. The materials can be platy materials such as talc, sericite, mica, synthetic mica, platy substrate coated with organic and inorganic molecules, bismuth oxychloride, barium sulfate. Particle can be composed of several materials (like dyes, lakes, toners). Lakes are, for example, dyes with aluminum hydroxide to help bind to solid. Color can be generated through fluorescence, absorption or iridescence. That is, color of modifier materials is generated through optical means rather than, for example, chemical means.

The optical modifier may also be a UV screen material with a $D_{50}$ <100 nanometers (where $D_{50}$ means size of 50% of particles or less is <100→m.

The optical modifiers may also be defined by their physical properties. For example, the optical modifier may be broadly defined as follows:
- i) an exterior surface having a refractive index of 1.3 to 4.0
- ii) a geometry which is spheroidal, platy or cylindrical
- iii) dimensions: spheroidal—0.1 to 200 μm, platy—1 to 200 μm, cylindrical—1 to 200 μm in length and 0.5 to 5.0 μm in diameter
- iv) a D50 of ≦200 microns in particle size.
- v) may have fluorescence color, absorption color and/or interference color (color through optics)

More specifically particles providing change in shine/glow/radiance may be defined as follows:
- i) an exterior surface having a refractive index of 1.8 to 4.0,
- ii) a geometry which is platy or cylindrical,
- iii) dimensions: spheroidal—0.1 to 200 μm (microns), platy—10 to 200 μm, cylindrical—10 to 200 μm in length and 0.5 to 5.0 μm in diameter, and
- iv) a D50 of ≦200 μm in particle size.

Particle providing skin lightening/color may be defined as follows:
- i) an exterior surface having a refractive index of 1.3 to 4.0,
- ii) a geometry which is spheroidal or platy,
- iii) dimensions: spheroidal—0.1 to 1 μm microns, platy—1 to 30 μm,
- iv) a D50 of ≦300 μm in particle size, and
- v) may have fluorescence color, absorption color and/or interference color (color through optics).

Particle-producing evenness or soft focus may be defined as follows:
- i) an exterior surface having a refractive index of 1.3 to 2.0,
- ii) a geometry which is spheroidal, platy or cylindrical,
- iii) dimensions: spheroidal—0.1 to 200 μm, platy—1 to 10 μm, cylindrical—1 to 10 μm in length and 0.5 to 5.0 μm in diameter, and
- iv) a D50 of ≦200 μm in particle size.

Of course, the formulation can contain a mixture of particles, each containing characteristics of a specific visual benefit, to create a combination of visual effects.

It is also to be understood that for visual effects/attributes to have maximum effect, the particles have to be well dispersed on the skin and should also give minimal to no sensory negatives.

By being "well dispersed" is meant that the particles should not agglomerate and that they should be spread easily through the skin surface.

In a preferred embodiment, less than 30% of particles $TiO_2$ and other optical modifiers are agglomerates having a size of ten times or more than the particle size. This can be measured using optical or electron microscopy.

The particle is used at about 0% to 35% by weight preferably 0.2 to 25% by wt., of the composition.

TITANIUM DIOXIDE

Compositions of the invention require use of titanium dioxide wherein particle size is sub-micron. Specifically, particle must be in the range 100 to 300 microns, preferably 120 to 300 nanometers.

The key aspect of the particle size requirement is to combine and balance out two optical effects. For particles with a size larger than 200 nm, one gets Mie light scattering. This light scattering mechanism scatters all the wavelengths in the visible spectrum creating a white, opaque effect. Such particle sizes are good for generating effective concealing hiding power and white color. Particles that are less than 200 nm in size create Rayleigh light scattering. This form of light scattering only scatters back blue light. The rest on the visible spectrum wavelengths are transmitted through. Such characteristics would create a bluish translucent effect, which would counter act the yellow color in the skin tone to produce a lighter, fairer visual effect. By combining the two light scattering mechanisms (and requiring the particle sizes used be in the range 100 to 300 microns), a balance between opacity and translucency, as well as whiteness and blueness, can be obtained to produce the desired visual appearance/effect sought.

The $TiO_2$ should be used at level of from about 0.01 to 30% preferably to 0.1 to 25% by wt.

DEPOSITION ENHANCEMENT

The deposition enhancement is key to the delivery of titanium dioxide and optical particles providing enhanced visual benefit (e.g., as defined in changes in )L, )a*, etc. and in methods to manipulate the values to provide the desired benefit, e.g. radiance, color, etc.).

In one embodiment, the deposition is provided by a deposition system comprising as follows:
 a) from about 0.1 to about 10% by wt., preferably 0.1 to 8% by wt. of a cationic polymer having change density $\geq 1$ Meq/gram, and
 b) about 0.1 to 30% by wt., preferably 0.5% to 25% by wt. of an anionic surfactant which forms a precipitate with cationic polymer upon dilution.

The precipitate formed can be a floc which can be broken up upon shear or rubbing to form a uniform and dispersed film on the surface of the skin.

Example of such surfactants include $C_{10}$-$C_{24}$ fatty acid soaps (e.g., laurates), alkyl taurate (e.g., cocoyl methyl taurate or other alkyl taurates), sulfosuccinates, alkyl sulfates, glycinates, sarcosinates and mixtures thereof.

It is important that the cationic have the noted charge in order to form the precipitate which is a key to the deposition of optical modifiers delivering the desired optical attributes.

The polymers may be modified polysaccharides including cationic guar gums, synthetic cationic polymers, cationic starches, etc.

Specific cationic polymers which are to be used include Merquat®) polymers such as polyquaternium 6 (e.g., Merquat®100 or Salcare®SC30) and polyquatrnium 7 (e.g. Merquat®2200 or Salcare®SC10); guar gums and/or derivatives (e.g. Jaguar C17); quaternized vinylpyrrolidone/methacrylate copolymers (e.g., Gafquat® 775); and polyquaternium-16 (e.g.; Luviquat®FC550)

In general, other deposition aids (e.g., for the $TiO_2$ and optional optical modifier particles) may include granular anionic polymers (e.g. alkaloid polymer such as starch, cellulose or their derivatives). That is if the deposition system additionally comprises such deposition aid, results are further enhanced.

Yet, another way to enhance deposition may be through modification (e.g. surface modification) of particles.

In another embodiment, the deposition enhancement system may comprise:
 1) from 0.1 to 10% by wt. of an anionic polymer having charge density of at least $\geq 1.0$ Meq/gram; and
 2) from about 0.1 to 30% cationic surfactant which forms a precipitate with the anionic polymer upon dilution.

This system is the inverse of cationic polymer anionic surfactant system. The precipitate can also be a floc which can be broken up on shear or rubbing and form a uniform and dispersed film on the skin surface.

Cationic surfactant may be a quaternary amino surfactant or an amphoteric such as betaine (e.g., cocoamidopropyl betaine).

The anionic polymer may be a polyacrylate, cross-linked polyacrylate, polyurethane and/or alkaloid derived polymer (e.g., starch, cellulose and derivatives), polysaccharide (e.g. xanthan gum), agar and/or mixtures thereof.

This system may also additionally comprise 0.1 to 30% granular anionic polymer which is natural alkaloid polymer (starch, cellulose and derivatives) as deposition aid.

EXAMPLES

Protocol

In Vitro Porcine/Pig Skin Assay

A piece of black porcine skin is used (L=40±3), where skin has dimensions of 5.0 cm by 10 cm, and the skin is mounted on black background paper card. Initial measurements of untreated skin are made. The mounted skin is then washed and rinsed with 0.2 g of liquid wash-off formulation or soap bar. After two (2) hours of drying, final measurements are made.

Color Measurements

Initial and final color measurements were made of porcine or in-vivo human skin using a Hunter Lab spectra colormeter using a 0° light source and 45° detector geometry. The spectra colormeter was calibrated with the appropriately black and white standards. Measurements were made before and after wash treatment. Three measurements were made each time and averaged. Values of L, a*, and b*, which came from the L a* b* color space representation, were obtained in this manner. L measures units of "Lightness", a* measures values from red to green and b* measures values from yellow to blue.

Reflectance (Gloss) Determination

Initial and final reflectance/radiance measurements of porcine or in-vivo human skin was made with a glossmeter which measures units of gloss. The glossmeter was first set with both detector and light source at 85° from normal. The glossmeter was calibrated with appropriate reflection standard. Measurements of gloss were taken before and after application of formulation and Δ gloss was calculated to obtain percent difference.

Opacity Determination

Opacity of washable deposition was calculated from Hunter Lab color measurements. Opacity contrast was calculated from ΔL (change in whiteness after deposition compared to prior to deposition) divided by 60 (which is the difference in L value of skin and a pure white color).

Examples 1-5

The following compositions show changes in value (i.e. Δ gloss (%), ΔL, Δa*, Δb*, as seen at bottom of chart) when surfactant and deposition systems are used relative to compositions either without same ingredients and/or with different or no deposition systems.

| Pigment-Containing Compositions | | | | | |
|---|---|---|---|---|---|
| | Ex. 1 | Ex. 2 | Ex. 3 | Ex. 4 | Ex. 5 |
| Component | | | | | |
| Lauric/Myristic/Palmitic/Stearic acid (fatty acids) | 3.27/5.37/7.12/6.24/3.91 KOH | | | | |
| Sodium N-cocoyl N-methyl taurate (30%) (surfactant) | 6.0 | | | | |
| 20Eocetylether/dipropyleneglycol/glycerin/maltitiol solution(75%) (sensory) | 4/8.8/12/4 | | | | |
| Dibutylhydroxytoluene/EDTA | 0.05/0.05 | | | | |
| Jaguar C13S (Cationic Polymer) | 0.4 | 0.4 | 0.4 | 0.4 | 0.4 |
| Titanium Dioxide (Kronos 2071-U) | 20 | 10 | 10 | 10 | 10 |
| Metal soap treated Talc (J68MT, <10 um, U.S. cosmetic Corporation) | — | — | 5 | — | — |
| Mica (TiO2 coated mica, <15 um, Timiron MP1005 from Rona) | — | — | — | 5 | — |
| Mica22 (22 um, Cardre Inc.) | — | — | — | — | 5 |
| Petrolatum | — | — | — | — | — |
| Neosil CP10 (Crossfield, silica gel 50 to 200 um as exfoliate) | — | — | — | — | — |
| Perfume | 0.25 | 0.25 | 0.25 | 0.25 | 0.25 |
| Deionized water | To 100 | To 100 | To 100 | To 100 | To 100 |
| Pig Skin invivo | | | | | |
| Δ gloss (%) | −39.8 | −20.8 | 0 | 16.6 | 34.3 |
| Δ L | 19.3 | 7.6 | 7.9 | 7.8 | 14.5 |
| Δ a* | −0.7 | −0.5 | −0.3 | −0.1 | −1.5 |
| Δ b* | −8.3 | −5.7 | −6.7 | −7.5 | −6.7 |

For 4 rows, same ratios used for all 5 examples.

As seen from the Table above, systems of the invention create optical attributes (ΔL, Δa*, etc.) which vary in change of the value (and accordingly with the attribute which is highlighted) depending on exact particle, size of particle, and deposition system used. Thus, applicants are able to manipulate values from a wash-off system; and to provide values and the ability to manipulate previously unknown.

A more detailed discussion of observations which can be made from the many examples is set forth below:

Examples 1 to 5, are Jaguar C13S based formulations, which show some deposition.

Examples 1 and 2 have 20% $TiO_2$ and 10% $TiO_2$, respectively, with the 20% TiO2 formulation showing higher deposition and larger ΔL change. There is also a large (and negative) change in the b* value (becoming bluer) The deposition also has a matting visual effect as can be seen from the negative Δgloss (which indicates a lowering of shine).

Examples 3 to 5 use Example 2 formulation with an addition of a reflective particle material.

Example 3 has talc ($D_{50}$ of 1 um) included into the formulation. The slight reflectivity of talc counteracts the matting effect of the deposited TiO2, as can be seen by the zero change in Δgloss. This combination gives a whiter, lighter appearance while still maintaining the skin's normal shine. The addition of the talc did not alter the ΔL or Δb* seen from Example 2.

Example 5 is the same as Example 3 except that natural mica ($D_{50}$ of 22 um) is used. The higher reflectivity of the larger sized mica counteracts the matting effect of the deposited $TiO_2$ and increases the visual shine, as can be seen by the increase in Δgloss. The addition of the natural mica did not alter the ΔL or Δb* seen from Example 2.

Example 4 is the same as Example 3 except that a titan coated mica ($D_{50}$ of 6 um) is used. The greater reflectivity of the titan-coated mica counteracts the matting effect of the deposited $TiO_2$ and increases the visual shine, as can be seen by the increase in Agloss. The addition of the coated mica does increase the ΔL or Δb* as compared to Example 2.

The control is for comparison purposes. It has the same formulation as Example 2 except there is no cationic polymer (Jaguar C13S). From the L, a*, b*, and gloss values, no deposition is observed.

From Examples 1 to 5, changes in visual attributes can be seen but they are not large enough. The particle deposition needs to be larger. For this to occur, a cationic polymer with a larger charge density must be used (in this case Merquat 100).

Example 6 is the same as Example 2, except the cationic polymer used is Merquat 100 instead of Jaguar. As can be seen from the ΔL and Δgloss, the deposition of the TiO2 is much greater (by a factor of 5). The visual effect is a much greater whiteness but also a larger increase in mattness. To counteract the mattness, natural mica or talc can be added to the formulations.

Examples 7 and 8 are Merquat 100 formulations with natural mica or talc. Both examples show an attenuation in the matting effect of the large TiO2 deposition as can be seen by the lower negative or even positive Δgloss relative to, for example, Example 6. Example 9 is a Merquat 100 formulation with Timiron super blue, an iridescent titania coated mica pigment. The example shows attenuation in the matting effect of the large $TiO_2$ deposition as can be seen by the positive Δgloss. It also crates a blue hue from the iridescent color.

Starch Structuring

The facial wash-off formulation can also use a different hydrophilic structural dispersent, such as starch. Similar correlations and trends can be seen with the starch formulation system as with the previous examples.

Example 12 and Example 13 compare the deposition of TiO2/talc from formulations using Merquat 100 and Jaguar C13S, respectively. As before, the higher charge density Merquat shows greater deposition than Jaguar, with similar visual attributes.

Example 10 is a control formulation, with no cationic polymer. From the L, a*, b*, and gloss measurements, there is little to no deposition.

Example 11 shows the importance of compatibility of surfactant systems to deposition efficiency. Example 11 uses a mixture of CAP Betaine and lauryl ether sulfate. In comparison with Example 12, the deposition is less efficient as seen from the lower ΔL values. This is an indication that the CAP Betaine/lauryl ether sulfate surfactant system is not as effective precipitating cationic polymer upon dilution.

Example 6

The chart below provides additional examples.

Pigment-Containing Compositions

| Component | Ex. 6 |
|---|---|
| Lauric acid | 3.27 |
| Myristic acid | 5.37 |
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Sorbitol | — |
| Maltitol solution (75%) | 4 |
| Dibutylhydroxytoluene | 0.05 |
| EDTA tetrasodium tetrahydrate | 0.05 |
| Jaguar C13S (Cationic Polymer) | — |
| Merquat 100 (Cationic Polymer) | 0.4 |
| Titanium Dioxide | 10 |
| UV TiO2 (Treated) | — |
| UV TiO2 (M212, Presperse) | — |
| Petrolatum | — |
| Perfume | 0.25 |
| Deionized water | To 100 |
| Pig skin in-vitro | |
| Δ gloss (%) | −50.0 |
| Δ AL | 34.6 |
| Δ a* | −2.4 |
| Δ b* | −8.6 |

Again, it can be seen from the above chart how deposition system and particles of invention provide compositions with desired values providing desired optical attributes (e.g., radiance, color, shine).

Control

The chart below provides additional examples.

| Component | Control |
|---|---|
| Lauric acid | 3.27 |
| Myristic acid | 5.37 |
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Maltitol solution (75%) | 4 |
| Dibutylhydroxytoluene | 0.05 |
| EDTA tetrasodium tetrahydrate | 0.05 |
| Jaguar C13S | 0 |
| Polymer JR | |
| Merquat 100 | — |
| Titanium Dioxide | 10 |
| Timiron Super blue | — |
| Petrolatum | — |
| Perfume | 0.25 |
| Deionized water | To 100 |
| Pig skin in-vitro | |
| Δ gloss (%) | −3.9 |
| Δ L | 0.1 |
| Δ a* | 0.1 |
| Δ b* | 0.1 |

Again it can be seen from the above control that when there is no cationic, there is little or no deposition.

Example 7

The chart below again shows different variations.

Pigment-Containing Compositions

| Component | Ex. 7 | Ex. 9 |
|---|---|---|
| Lauric acid | 3.27 | 3.27 |
| Myristic acid | 5.37 | 5.37 |
| Palmitic acid | 7.12 | 7.12 |
| Stearic acid | 6.24 | 6.24 |
| Potassium hydroxide | 3.91 | 3.91 |
| Sodium N-cocoyl N-methyl taurate (30%) | 6.0 | 6.0 |
| Polyoxyethylene cetylether(20E.O.) | 4 | 4 |
| Dipropylene glycol | 8.8 | 8.8 |
| Glycerin, concentrated | 12 | 12 |
| Maltitol solution (75%) | 4 | 4 |
| Dibutylhydroxytoluene | 0.05 | 0.05 |
| EDTA tetrasodium tetrahydrate | 0.05 | 0.05 |
| Jaguar C13S | — | 0.4 |
| Merquat 100 | 0.8 | — |
| Titanium Dioxide (PW liquid TiO2, 0.3 um) | 10 | — |
| UV TiO2 (M212) | — | — |
| Mica (TiO2 coated mica, <50 um, Timiron super blue from Rona) | — | 5 |
| Mica22 (22 um, Cardre Inc.) | 5 | — |
| Petrolatum | — | — |
| Perfume | 0.25 | 0.25 |
| Deionized Water | To 100 | To 100 |
| Pig skin in-vitro | | |
| Δ gloss (%) | 20.0 | +4.96 |
| L | 33.03 | +8.35 |
| A* | −3.8 | =0.39 |
| B* | −9.55 | −7.35 |

Example 8

The chart below shows one more example.

| Component | Ex. 8 |
|---|---|
| Lauric acid | 3.27 |
| Myristic acid | 5.37 |

-continued

| Component | Ex. 8 |
|---|---|
| Palmitic acid | 7.12 |
| Stearic acid | 6.24 |
| Potassium hydroxide | 3.91 |
| Sodium N-cocoyl N-methyl taurate (30%) | 6.0 |
| Polyoxyethylene cetylether(20E.O.) | 4 |
| Dipropylene glycol | 8.8 |
| Glycerin, concentrated | 12 |
| Maltitol solution (75%) | 4 |
| Dibutylhydroxytoluene | 0.05 |
| EDTA tetrasodium tetrahydrate | 0.05 |
| Merquat 100 | 0.4 |
| Titanium Dioxide | 10 |
| Soft Talc | 5 |
| DI Water | To 100 |
| Petrolatum | 10 |
| Perfume | 0.25 |
| DI water | To 100 |
| Pig skin in-vitro | |
| Δ gloss (%) | −5.6 |
| L | 31.3 |
| A* | −3.6 |
| B* | −8.0 |

The −5.6 shows a somewhat neutral gloss counteracts the matting effect of the Titanium dioxide.

Examples 10-13

The chart below shows examples with Starch Structured liquids.

| Component | Ex. 10 | Ex. 11 | Ex.12 | Ex.13 |
|---|---|---|---|---|
| K Laurate | 6 | — | 6 | 6 |
| Na cocoyl methyl taurate | 3 | — | 3 | 3 |
| Lauryl ether sulfate | 0 | 6 | 0 | 0 |
| Cocoamidoprogyl Betaine | — | 3 | — | — |
| Corn starch | 10 | 10 | 10 | 10 |
| Structure XL Co-water soluble cross-linked starch | 1.5 | 1.5 | 1.5 | 1.5 |
| Glycerin | 6 | 6 | 6 | 6 |
| Jaguar C135 | — | — | — | 0.4 |
| Merquat 100 | — | 0.4 | 0.4 | — |
| TiO2 | 15 | 15 | 15 | 15 |
| Soft Talc | 5 | 5 | 5 | 5 |
| Petrolatum | 5 | 5 | 0 | 0 |
| Sunflower seed oil | — | — | — | — |
| Pig skin in-vitro | | | | |
| Δ gloss (%) | −21.4 | −24.6 | −26.4 | 0.0 |
| L | 4.7 | 21.3 | 44.3 | 15.7 |
| A* | −0.5 | −5.2 | −5.8 | −4.23 |
| B* | 4.0 | 10.9 | −10.6 | −11.0 |

We claim:

1. A rinse-off cleanser composition for delivering enhanced opacity (defined by ΔL value) while minimizing matting effect (lower shine), which composition consisting of:
   (a) from about 0.5% to about 90% of by wt. surfactant system comprising $C_{10}$-$C_{24}$ fatty acids, alkyl taurates, and oxyalkylene ethers;
   (b) from 0.1 to 35% by wt. of solid particulate optical modifier, said modifier selected from the group consisting of talc, mica having particle size below about 50 micrometers and mixtures thereof;
   (c) from 0.01% to 30% by wt. of a titanium dioxide particle having size of about 100 nm to 300 nm;
   (d) from 2 to 25% by wt. of a deposition enhancement system, wherein, the deposition enhancement system comprises (i) 0.1 to 10% by wt. polyquaternium 6 cationic polymer or polymers having charge density of about 6.2 meq/g and (ii) 0.1 to 30% by wt. anionic surfactant and optionally (iii) about 0.1 to 30% by wt. of a granular anionic polymer which is a natural alkaloid polymer which forms a precipitate with said cationic polymer or polymers upon dilution, said anionic forming the precipitate being selected from the group consisting of $C_{10}$ to $C_{24}$ fatty acid soaps, alkyl taurates, and mixtures thereof; and
   (e) from about 0.1% to 45% of a hydrophilic structural dispersant comprising polyalkylene glycol, maltitol and glycerin, wherein the combination of titanium dioxide having specified particle size as set forth in (c) and of optical modifier (b) together with deposition enhancement system of (d) provides at least 5% enhancement in ΔL while simultaneously enhancing shine effect, said enhancement of shine defined by a more positive Δgloss value compared to absence of said optical modifier of (b).

2. A composition according to claim 1, comprising 20% to 75% by wt. surfactant.

3. A composition according to claim 1, comprising 0.2% to 25% by wt. optical modifier.

4. A composition according to claim 1, wherein the precipitate of (d) is a floc which can be broken upon shear or rubbing to form a uniform and dispersed film on surface of skin.

5. A composition according to 1, wherein said polymer is starch and derivatives, cellulose and derivatives and mixtures thereof.

6. A composition according to claim 1, wherein the particles are dispersed on the skin in that less than 30% of the particles have a size of 10 times or more than the $D_{50}$ particle size as measured by optical microscopy.

7. A rinse-off cleanser composition for delivering enhanced opacity (defined by ΔL value) while minimizing matting effect (lower shine), which composition consisting of:
   (a) from about 0.5% to about 90% of by wt. soap and optionally a taurate;
   (b) from 0.1 to 35% by wt. of solid particulate optical modifier, said modifier selected from the group consisting of talc, mica and mixtures thereof;
   (c) from 0.01% to 30% by wt. of a titanium dioxide particle having size of about 100 nm to 300 nm;
   (d) from 2 to 25% by wt. of a deposition enhancement system, wherein, the deposition enhancement system comprises (i) 0.1 to 10% by wt. polyquaternium 6 polymer or polymers having charge density of about 6.2 meq/g and (ii) 0.1 to 30% by wt. anionic surfactant which forms a precipitate with said cationic polymer or polymers upon dilution, said anionic forming the precipitate being selected from the group consisting of soap, alkyl taurate and mixtures thereof; and
   (e) from about 0.1% to 45% of a hydrophilic structural dispersant comprising glycerin and starch, wherein the combination of titanium dioxide having specified particle size as set forth in (c) and of optical modifier (b) together with deposition enhancement system of (d) provides at least 5% enhancement in ΔL while simultaneously enhancing shine effect, said enhancement of shine defined by a more positive Δgloss value compared to absence of said optical modifier of (b).

* * * * *